(12) United States Patent
Aga et al.

(10) Patent No.: US 10,987,018 B2
(45) Date of Patent: Apr. 27, 2021

(54) METHOD AND SYSTEM FOR DETERMINING BODY IMPEDANCE

(71) Applicant: Vital Connect, Inc., San Jose, CA (US)

(72) Inventors: Arshan Aga, San Jose, CA (US); Steve Fang, San Jose, CA (US)

(73) Assignee: VITAL CONNECT, INC., San Jose, CA (US)

(*) Notice: Subject to any disclaimer, the term of this patent is extended or adjusted under 35 U.S.C. 154(b) by 876 days.

(21) Appl. No.: 15/687,923

(22) Filed: Aug. 28, 2017

(65) Prior Publication Data
US 2019/0059777 A1 Feb. 28, 2019

(51) Int. Cl.
*A61B 5/053* (2021.01)
*A61B 5/08* (2006.01)
*A61B 5/00* (2006.01)
*A61B 5/0537* (2021.01)

(52) U.S. Cl.
CPC ............ *A61B 5/053* (2013.01); *A61B 5/0537* (2013.01); *A61B 5/0809* (2013.01); *A61B 5/7203* (2013.01); *A61B 5/7225* (2013.01); *A61B 5/4878* (2013.01); *A61B 5/725* (2013.01)

(58) Field of Classification Search
CPC ..... A61B 5/053; A61B 5/0537; A61B 5/4878; A61B 5/0531; A61B 5/0535
See application file for complete search history.

(56) References Cited

U.S. PATENT DOCUMENTS 9,204,816 B2 * 12/2015 Aga .................... A61B 5/0537

* cited by examiner

*Primary Examiner* — Carrie R Dorna
(74) *Attorney, Agent, or Firm* — Brundidge & Stanger, P.C.

(57) ABSTRACT

A method and system for determining a body impedance ($Z_{body}$) of a user are disclosed. The method comprises coupling a sensor device to the user, wherein the sensor device includes at least a first and a second electrode. The method includes applying a voltage signal ($V_{in}$) through a first impedance ($Z_{in1}$) to the first electrode and through a second impedance ($Z_{in2}$) to the second electrode to produce an output signal. The method includes measuring a differential voltage ($V_{body}$) across the first and second electrodes and calculating the body impedance ($Z_{body}$) using the measured differential voltage ($V_{body}$), the voltage signal ($V_{in}$), the first impedance ($Z_{in1}$), and the second impedance ($Z_{in2}$).

10 Claims, 5 Drawing Sheets

METHOD AND SYSTEM FOR DETERMINING BODY IMPEDANCE

FIELD OF THE INVENTION

The present invention relates to sensor devices, and more particularly, to a method and system for determining body impedance using a sensor device.

BACKGROUND

Approximately 60% of an average person's body weight is composed of water. A person's body weight composition varies due to a variety of factors including age, diet, weight, and gender. Despite these variations, the majority of a person's body weight composition is made up of water. Physiologically, "body water" or "hydration level" are terms utilized to describe the water content of the body. A person's hydration level can be described in liters or as a percentage of the person's total body weight.

Maintaining a reasonable and healthy hydration level is crucial to the overall health of a person. Additionally, even small decreases in a person's hydration level can significantly affect athletic performance levels. Conventional methods of testing a body's hydration level include monitoring body mass changes and testing blood and urine for various markers. However, these conventional methods are inefficient, costly and require time consuming laboratory analysis to arrive at the proper hydration level.

These issues limit the monitoring of a person's hydration level. Therefore, there is a strong need for a cost-effective solution that overcomes the above issues by non-invasively calculating body impedance in real-time using sensor devices to enable the monitoring of health related values.

Local fluid status is also a useful metric to track. A determination of fluid buildup in lungs could be used in diagnosing or predicting pneumonia as well as addressing the need in Chronic Heart Disease (CHF) patients to determine whether a diuretic should be administered.

Respiratory rate and respiratory volume are very important vital signs. They can be used to determine a health of an individual and potentially diagnose certain ailments. Respiratory rate and respiratory volume can also be used as a predictive measure and determine whether the health of an individual is improving or deteriorating.

Body composition is also a useful parameter in determining the health of a patient. Determining a person's body composition (i.e. the percentage of fat, muscle, etc) is commonly tracked and used for determining overall health. Tracking changes in a person's body composition is useful in many applications including weight loss.

One vital sign that can be used on its own or in combination with other vital signs to determine hydration level, local fluid status, respiratory rate, respiratory volume and body composition is bio-impedance. The present invention addresses these needs.

SUMMARY OF THE INVENTION

A method and system for determining a bio-impedance ($Z_{body}$) of a user are disclosed that includes measuring a first voltage across a first impedance after performing a first mixing operation using a clock signal or sine wave; measuring a second voltage across the first impedance after performing a second mixing operation using a 90-degree phase shifted clock signal or cosine wave; measuring a third voltage at an output after performing a third mixing operation using the clock signal or sine wave; measuring a fourth voltage at the output after performing a fourth mixing operation using the 90-degree phase shifted clock signal or cosine wave; and processing the measured first through fourth voltages and the first impedance to calculate a bio-impedance.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

Figure 1A:
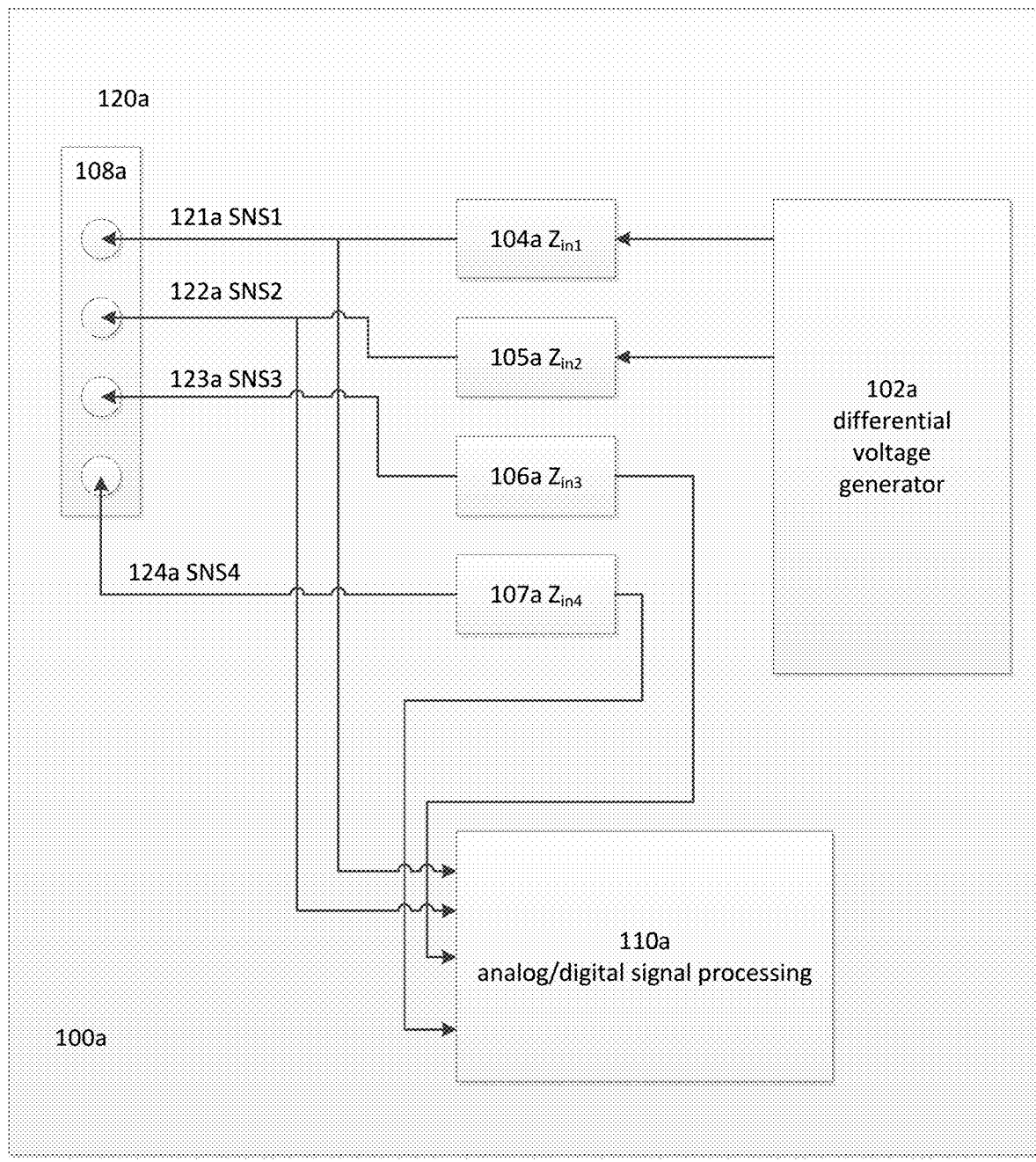
FIG. 1a illustrates a differential system in accordance with an exemplary embodiment.

The present invention relates to sensor devices, and more particularly, to a method and system for determining body impedance using a sensor device. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A method and system in accordance with the present invention allows for the measurement of a user's body impedance using a sensor device. One of ordinary skill in the art readily recognizes that a variety of sensor devices may be utilized including wireless sensor devices with embedded circuitry and that would be within the spirit and scope of the present invention. By connecting a portable sensor device to the user through two or more sensor nodes or electrodes and stimulating these sensor nodes with an electrical signal through a known impedance, a resultant electrical output signal at the sensor nodes is detected by the portable sensor device. The resultant electrical output signal is processed using a combination of analog and digital signal processing to determine the impedance of the user's body or body impedance ($Z_{body}$).

The determined bio-impedance ($Z_{body}$) is further processed using a hardware and/or software approach to determine a health related value such as the hydration level, respiratory rate, respiratory volume, body composition or local fluid status of the user. One of ordinary skill in the art readily recognizes that the calculated bio-impedance can be utilized for measuring and/or monitoring a variety of health related values including but not limited to a person's hydration levels and respiratory rates and that would be within the spirit and scope of the present invention.

In one embodiment, the impedance from one location of a user's body to another location of the user's body, or body impedance, is known as $Z_{body}$. $Z_{body}$ is inversely proportional to the level of hydration per the following equation:

$$\text{Hydration Level } \alpha \; 1/Z_{body}.$$

Using this inverse relationship, $Z_{body}$ is converted into a user's hydration level through hardware configurations and/or software algorithms that include other variables such as age, height, race, diet, weight, and gender. $Z_{body}$ is measured by injecting an input voltage signal ($V_{in}$) through a known impedance ($Z_{in}$) and through two or more electrodes into the user's body which has an unknown body impedance ($Z_{body}$). Given that $V_{in}$ and $Z_{in}$ are known values and that the voltage ($V_{body}$) across $Z_{body}$ can be measured by a sensor device, $Z_{body}$ is the only unknown value that needs to be calculated per the following equation:

$$Z_{body} = (V_{body}/(V_{in} - V_{body})) \times Z_{in}.$$

In one embodiment, the change in the calculated $Z_{body}$ value is utilized to measure respiration rate and respiration depth. When a person inhales and air fills up the lungs, the impedance across the person's lungs increases. When the person exhales and there is less air in the lungs, the impedance across the person's lungs decreases. By placing two or more electrodes on a user's body around the lungs, the voltage ($V_{body}$) across $Z_{body}$ can be measured by a sensor device once again to allow for the calculation of $Z_{body}$. $Z_{body}$ is directly proportional to the air in the lungs per the following equation:

$$\text{Air in Lungs } \alpha \; Z_{body}.$$

One of ordinary skill in the art readily recognizes that the input voltage signal ($V_{in}$) can be a variety of types of signals including but not limited to a single ended signal, a differential signal that can be inputted at different locations on the user's body, or a differential signal that can be inputted at different times or simultaneously and that would be within the spirit and scope of the present invention. Additionally, one of ordinary skill in the art readily recognizes that the input voltage signal ($V_{in}$) can be inputted on multiple electrodes which would create multiple differential voltages requiring additional calculations to find $Z_{body}$ and that would be within the spirit and scope of the present invention.

One of ordinary skill in the art readily recognizes that the known impedance ($Z_{in}$) can be a variety of impedances including but not limited to any combination of resistors, capacitors, inductors, switches, and transformer elements either in series or in parallel combinations to form an impedance that is deterministic in nature and that would be within the spirit and scope of the present invention.

To measure $Z_{body}$ more accurately, one of ordinary skill in the art readily recognizes that the input voltage signal ($V_{in}$) can be a sine wave, square wave, or a pulsed signal with fast rise and fall times that are less than 50 nanoseconds (ns) to reduce and make negligible the impedance of the two or more electrodes and that would be within the spirit and scope of the present invention.

As mentioned before, the resultant electrical output signal is processed to remove noise and/or artifacts such as bodily movements using a variety of hardware and/or software approaches including but not limited to a processing unit with circuits that perform functions such as rectification, absolute value, sample-and-hold, and track-and-hold. The processing unit can be a separate device coupled to the portable sensor device or can be entirely and/or partially embedded within the portable sensor device. These circuits may cause transitions or glitches in the output signal produced when the input voltage signal ($V_{in}$) or a circuit clock transitions. One of ordinary skill in the art readily recognizes that a common analog circuit block can be used after these circuits to reduce and/or eliminate the effects of these glitches or transitions and that would be within the spirit and scope of the present invention.

One of ordinary skill in the art readily recognizes that the common analog circuit block can be a variety of devices including but not limited to a filter that suppresses sharp transitions or a sampling circuit that has a clock with correct phase and/or correct duty cycle so the glitches or transitions are not detected by subsequent circuit blocks and that would be within the spirit and scope of the present invention. Additionally, one of ordinary skill in the art readily recognizes that the clock within each circuit block of the processing unit can have a variety of features including but not limited to programmable phase shifts, being phase shifted with respect to one another, and being non-overlapping with respect to one another through phase shifting, duty cycle alterations, or programmability and that would be within the spirit and scope of the present invention.

In addition to the glitches or transitions in the output signal, one of ordinary skill in the art readily recognizes that the processing unit can experience a variety of circuit non-idealities including but not limited to voltage driver pull-up and pull-down impedances and/or transition times being mismatched, a duty cycle of the voltage driver pull-up and pull-down not being ideal, the voltage driver not being completely differential due to a mismatch or by design, offsets in the various circuit blocks, and various circuit clocks being out of phase due to variations or by design and that would be within the spirit and scope of the present invention. These circuit non-idealities can be overcome by performing analog and/or digital processing including but not limited to circuit calibrations, adding switches, and programmatically altering any of the circuit blocks and that would be within the spirit and scope of the present invention.

The body impedance ($Z_{body}$) can be used to determine the absolute level of hydration in the user and/or to determine a relative level of hydration in the user. Determining a relative level of hydration in the user enables variations above certain thresholds to signify changes in the condition of the user between various levels including but not limited to slightly dehydrated, moderately dehydrated, severely dehydrated, and over-hydrated and that would be within the spirit and scope of the present invention.

To describe the features of the present invention in more detail, refer now to the following description in conjunction with the accompanying Figures.

FIG. 1a illustrates a differential system 100a in accordance with a first embodiment. The differential system 100a includes a differential voltage generator 102a; a first impedance unit 104a ($Z_{in1}$), a second impedance unit 105a ($Z_{in2}$), a third impedance unit 106a ($Z_{in3}$), and a fourth impedance unit 107a ($Z_{in4}$). Zin1 and Zin2 are coupled to the differential voltage generator 102a; Zin3 and Zin4 are coupled to the analog/digital signal processing unit 110a; electrodes 108a of the sensor device 120a with a first electrode (SNS1) 121a coupled to the first impedance 104a, a second electrode (SNS2) 122a coupled to the second impedance 105a, a third electrode (SNS3) 123a coupled to the third impedance 106a, and a fourth electrode (SNS4) 124a coupled to the fourth impedance 107a; and an analog/digital signal processing unit 110a coupled to the electrodes 108a of the sensor device 120a through Zin3 and Zin4.

One of ordinary skill in the art readily recognizes that the differential system 100a can utilize two impedance units and electrodes, four impedance units and electrodes, or more than four impedance units and electrodes and that would be within the spirit and scope of the present invention. Additionally, one of ordinary skill in the art readily recognizes that electrodes 108a and the sensor device 120a may be integrated together in a single device and that would be within the spirit and scope of the present invention. Additionally, one of ordinary skill in the art readily recognizes that the differential system 100a can utilize a variety of voltage sources including but not limited to voltage generators and current sources and that would be within the spirit and scope of the present invention.

The electrodes 108a of the sensor device 120a is coupled to, placed on, or removably attached to a user of the system 100a. The differential voltage generator 102a provides stimulus to the user through the electrodes 108a. In one embodiment, the differential voltage generator 102a transitions from a high voltage level to a low voltage level. One of ordinary skill in the art readily recognizes that the differential voltage generator 102a high and low voltage levels can be accomplished in a variety of ways including but not limited to a supply and ground voltage, a battery and ground voltage, or a positive and negative supply and that would be within the spirit and scope of the present invention.

Additionally, one of ordinary skill in the art readily recognizes that the differential voltage generator 102a high and low voltage levels can be accomplished by deriving two voltage levels from a positive supply or battery and a negative supply or ground through any combination of the means of regulation, charge pump regulation, voltage division or a ground derived through means such as regulation or voltage dividers and that would be within the spirit and scope of the present invention.

In one embodiment, the stimulus provided by the differential voltage generator 102a is a square or pulse wave with a frequency of 1 megahertz (MHz) with sharp transition times between the high voltage level and the low voltage level. One of ordinary skill in the art readily recognizes that the stimulus provided by the differential voltage generator 102 can also be a sine or cosine wave. This sine or cosine wave may also be generated through a digital-to-analog converter (DAC). This generator may include a filter in order to get a better signal quality. One of ordinary skill in the art readily recognizes that the stimulus can be a variety of other frequencies including but not limited to frequencies greater than 1 kilohertz (kHz) and can be a variety of other types of waves that exhibit sharp transition times that are less than 50 ns and that would be within the spirit and scope of the present invention.

In one embodiment, the voltage generator 102a may have a clock input to generate the waveform. This may be the case if a square wave is used or if a digital-to-analog converter is used. If a clock is used, the same clock can be used to generate the sine and cosine waveforms (or alternatively the clock and 90 degree phase shifted clock. The clock used to generate the sine and cosine waveforms (or alternatively the clock and 90 degree phase shifted clock) may be in phase with the clock used for the differential voltage generator or may be a known phase shift from the clock used for the differential voltage generator. This is important in achieving an accurate calculation of the body impedance.

The impedance Zin1, Zin2, Zin3 and Zin4 may consist of but are not limited to a series or parallel combination of passive analog components including resistors, capacitors, inductors, transformers. In some embodiments one may choose to not put any passive components and Zin1, Zin2, Zin3 or Zin4 will be a short circuit and therefore a direct connection to the electrode. In some embodiments Zin1 and Zin2 will include resistors. In some embodiments Zin1 and Zin2 will include capacitors. In some embodiments it will include a series combination of resistors and capacitors. These are three examples of impedances that may be used but the patent should not be limited to these three examples, any combination of passive components may be used.

A differential voltage is sensed by the, third, and fourth electrodes SNS3 123a, and SNS4 124a, as well as across Zin1 or Zin2 of the sensor device 120a or alternatively across the third and fourth electrodes as well as across the first and second electrode due to a voltage divider created between the first and second, impedances 104a and 105a, the contact impedance of the electrodes 108a to the body and the bio-impedance of the user. The differential voltage is processed by the analog/digital signal processing unit 110a utilizing analog and/or digital processing functions which results in a resultant value. One of ordinary skill in the art readily recognizes that a variety of analog and/or digital processing functions can be utilized including but not limited to a rectifier, an absolute value=|x|, a squaring function=$x^2$, sampling, sample-and-hold, track-and-hold, analog filtering, analog equalization, amplification, digitizing with an analog-to-digital converter, digital filtering, digital amplification, artifact removal, and baseline wander removal and that would be within the spirit and scope of the present invention.

In another embodiment, one of ordinary skill in the art readily recognizes that the differential voltage can also be sensed in a two electrode sensor device 120a by the first and second electrodes SNS1 121a and SNS2 122a of the electrodes 108a of the sensor device 120a due to a voltage divider created between the first and second impedances 104a and 105a, the contact impedance of the electrodes to the body of the user and the bio-impedance of the user.

One of ordinary skill in the art readily recognizes that the resultant value of the differential voltage post processing represents the bio-impedance that is inversely proportional to the level of hydration or level of water in the user's body and that would be within the spirit and scope of the present invention.

Figure 1B:
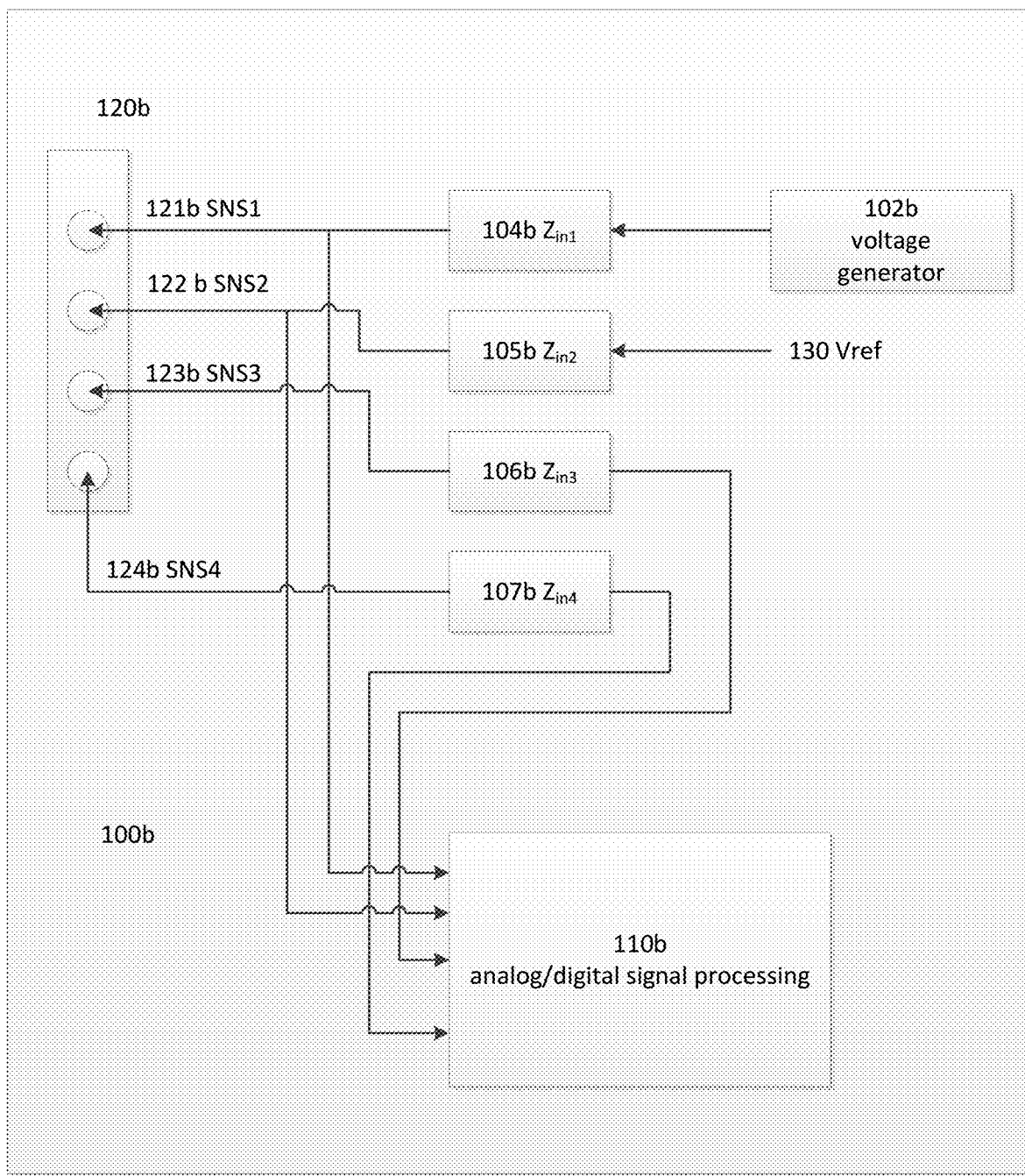
FIG. 1b illustrates a single-ended system in accordance with an exemplary embodiment.

FIG. 1b illustrates a single-ended system 100b in accordance with a first embodiment. The single-ended system 100b includes a voltage generator 102b; a first impedance unit 104b ($Z_{in1}$) coupled to the voltage generator 102b, a second impedance unit 105b ($Z_{in2}$) coupled to a reference voltage ($V_{ref}$), a third impedance unit 106b ($Z_{in3}$) and a fourth impedance unit 107b ($Z_{in4}$); Zin3 and Zin4 are coupled to the analog/digital signal processing unit 110b; electrodes 108b of the sensor device 120b with a first electrode (SNS1) 121b coupled to the first impedance 104b, a second electrode (SNS2) 122b coupled to the second impedance 105b, a third electrode (SNS3) 123b coupled to the third impedance 106b, and a fourth electrode (SNS4) 124b coupled to the fourth impedance 107b; and an analog/digital signal processing unit 110b coupled to the electrodes 108b of the sensor device 120b through Zin3 and Zin4.

Accordingly, the single-ended system 100b resembles the configuration of the differential system 100a except that in the single-ended system 100b, the voltage generator 102b inputs a voltage square, pulse wave, sine wave, or cosine wave into the first electrode (SNS1) 121b of the electrodes 108b of the sensor device 120b while the second electrode (SNS2) 122b of the electrodes 108b of the sensor device 120b is held at a constant reference voltage ($V_{ref}$) 131.

Current flows in and out of the second electrode of the electrodes 108b of the sensor device 120b that is held at $V_{ref}$. Based on a voltage divider between the first and second impedances 104b and 105b and the voltage across the electrodes 108b of the sensor device 120b, the bio-impedance ($Z_{body}$) is calculated. Further, output from the voltage generator 102b is connected to Zin1 104b, Vref 130 is connected to Zin2 105b. Zin3 106b and Zin4 107b are in series with the inputs Zin1 104b and Zin2 105b to block 110a. Zin3 106b and Zin4 107b are not connected to Vref 130 or the voltage generator 102b. The differential voltage will come from the electrodes SNS3 123b and SNS4 14b, connected to Zin3 and Zin4 and then connected to 110b.

Figure 2A:
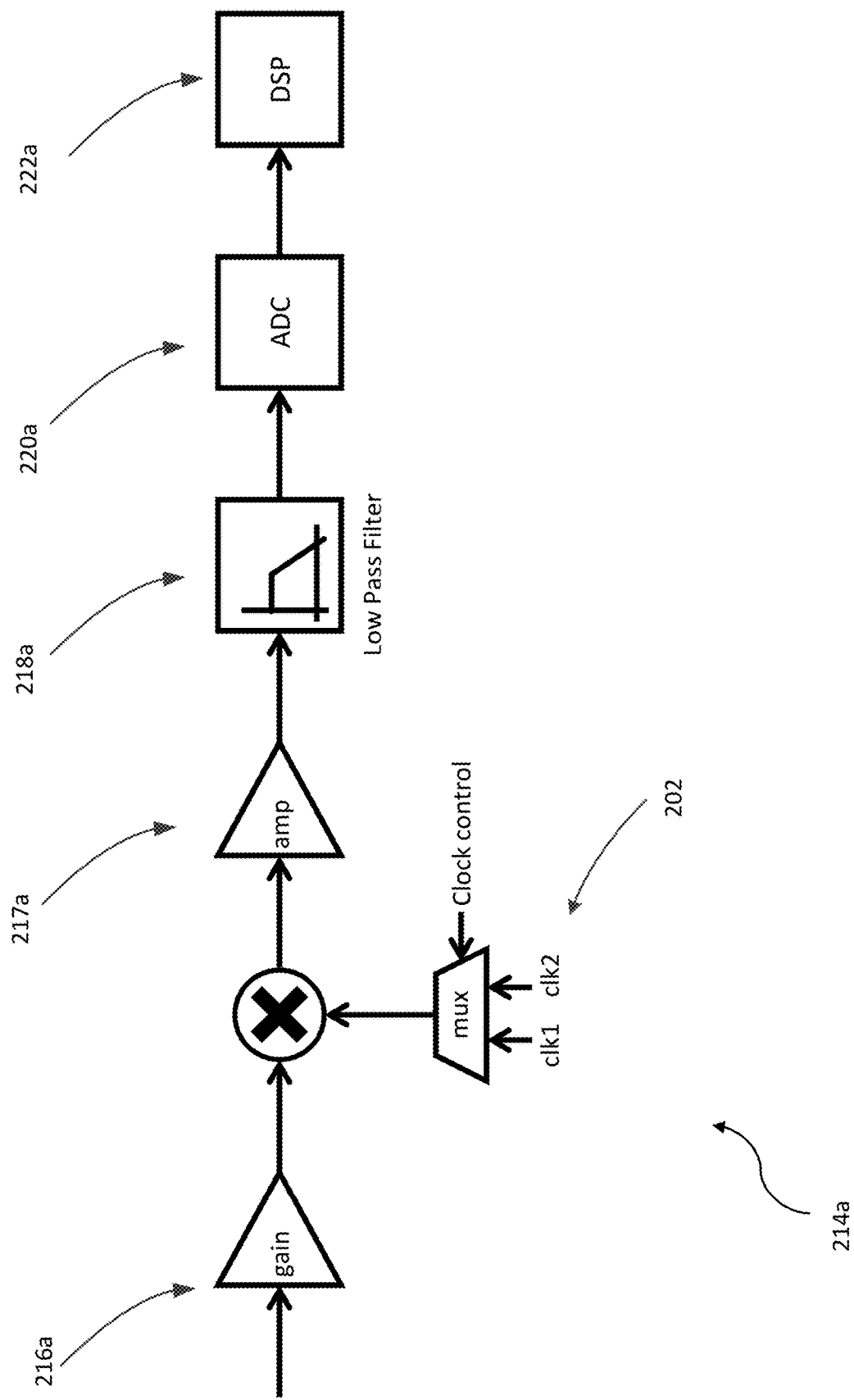
FIG. 2a illustrates a bio-impedance front-end receiver in accordance with an exemplary embodiment.

FIG. 2a illustrates an embodiment of an bio-impedance front-end receiver 214a. The bio-impedance front-end receiver 214a includes a gain 216a coupled to a mux 202, which is coupled to an amplifier (amp) 217a, which is coupled to a low pass filter (LPF) 218a, which is coupled to an analog-to-digital converter (ADC) 220a, which is coupled to a digital signal processor (DSP) 222a. One of ordinary skill in the art readily recognizes that the gain 216a, LPF 218a, ADC 220a, and DSP 222a can include a variety of configurations and that would be within the spirit and scope of the present invention.

In one embodiment, the voltage generator will have a clock input to generate the waveform. This may be the case if a square wave is used or if a digital-to-analog converter is used. If a clock is used, the same clock can be used to generate the sine and cosine waveforms (or alternatively the clock and 90 degree phase shifted clock) shown in FIG. 2a (block 202). The clock used to generate the sine and cosine waveforms (or alternatively the clock and 90 degree phase shifted clock) may be in phase with the clock used for the differential voltage generator or may be a known phase shift from the clock used for the differential voltage generator. This is important in achieving an accurate calculation of the body impedance.

Figure 2B:
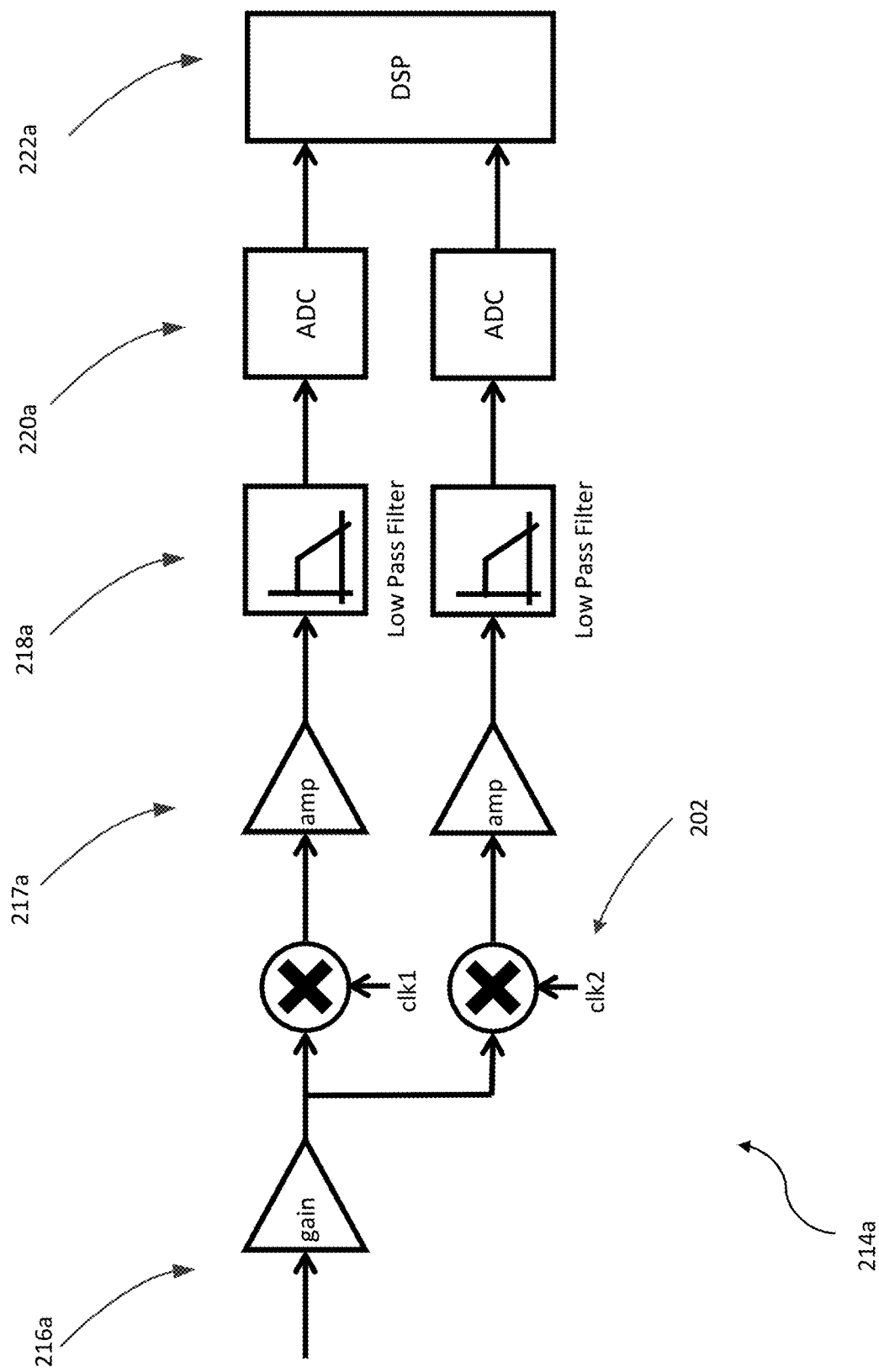
FIG. 2b illustrates a quadrature demodulation and trigonometric algorithm and operation.

The bio-impedance front-end receiver 214a implements IQ-demodulation. The demodulation decomposes the main signal to I and Q components which are samples of the main signal taken 90 degrees out of phase. Through a computer implemented quadrature demodulation and trigonometric algorithm and operation, the magnitude and phase is determined as depicted in FIG. 2b. As depicted in FIG. 2b, everything above a low frequency is filtered meaning that harmonics and other signals that are generated as a result of the mixing operation are attenuated by the filter. The Magnitude is equal to the square root of $(\alpha^2+\beta^2)=A/2$ (diff=>Mag=A). And the Angle=arctan ($\beta/\alpha$).

The operation is performed sequentially and therefore uses a single path for a single mixer to minimize the mismatch. Using dual mixers with a relative small area would have the additional issue of introducing mismatches which can cause errors in the system. Even though some of the mismatches will be up-converted to a higher frequency, large mismatches including large offsets cannot be filtered out completely given the certain bandwidth that is trying to be achieved. Therefore, single path is used for the single mixer and the two phases of clocks are multiplexed in, removing many sources of mismatch.

By keeping the mixer single path, the complicated mismatch and offset correction to keep the mismatch relatively small between the two mixers is avoided. The I and Q signals are needed to calculate the magnitude and is achieved by multiplexing in the sine wave or cosine wave (or clock signal and 90-degree phase shifted clock signal) into the mixer.

Figure 2C:
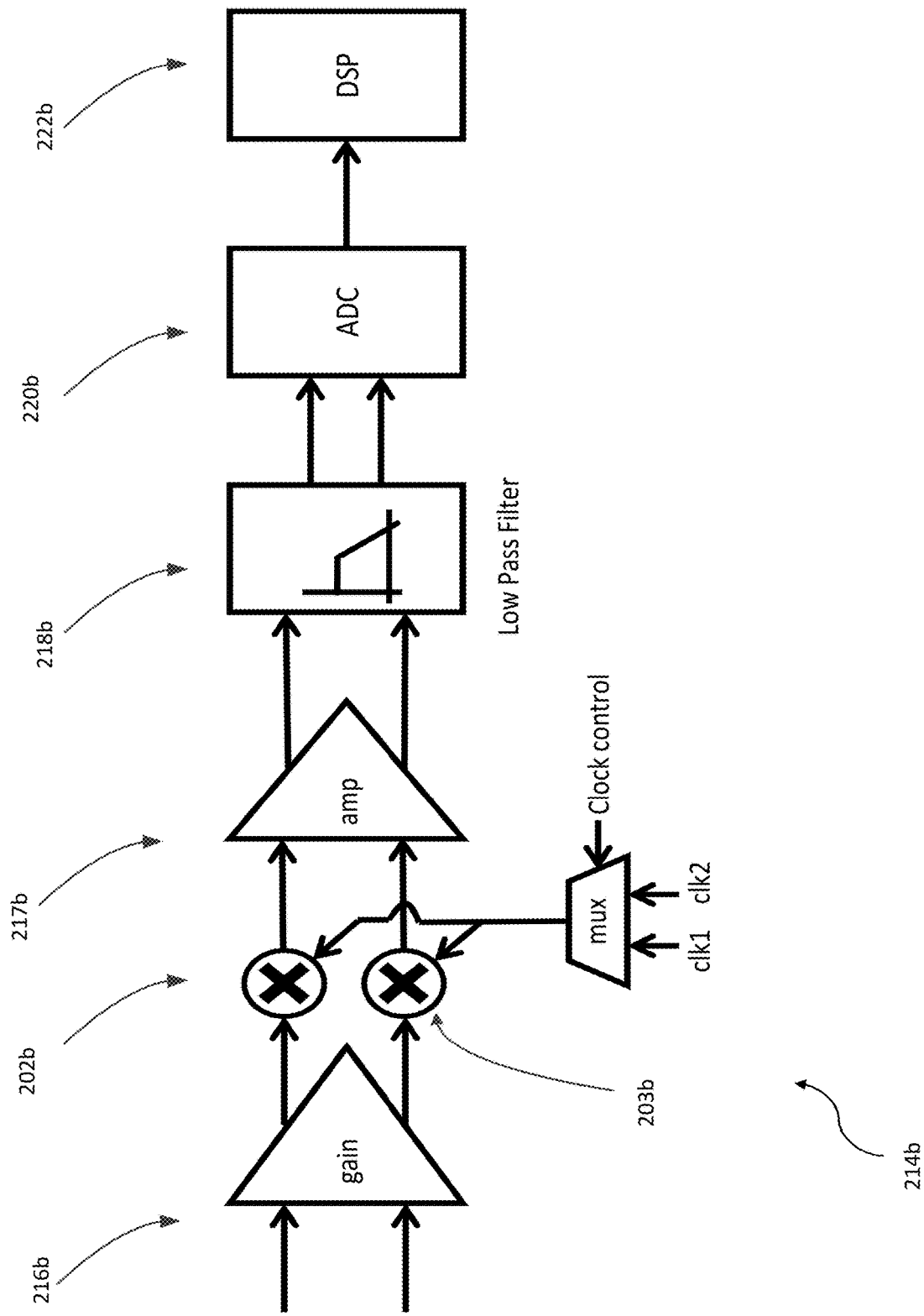
FIG. 2c illustrates a bio-impedance front-end receiver in accordance with an exemplary embodiment.

FIG. 2c illustrates a bio-impedance front-end receiver 214b. The bio-impedance front end receiver 214b includes a gain 216b coupled to mux 202b and mux 203b, which are coupled to an amplifier (amp) 217b, which is coupled to a low pass filter (LPF) 218b, which is coupled to an analog-to-digital converter (ADC) 220b, which is coupled to a digital signal processor (DSP) 222b. One of ordinary skill in the art readily recognizes that the gain 216b, LPF 218b, ADC 220b, and DSP 222b can include a variety of configurations and that would be within the spirit and scope of the present invention.

In one embodiment, gain 216b includes a first input (IP), a second input (IM), a first output (OP), a second output (OM), and a second clock (CK2). The LPF 218b includes a first input (IP), a second input (IM), a first output (OP), and a second output (OM). The ADC 220b includes a first input (IP), a second input (IM), an output (OUT [N:1]), and a third clock (CK3). The DSP 222b includes an input (IN) and an output (OUT).

In one embodiment, the voltage generator will have a clock input to generate the waveform. This may be the case if a square wave is used or if a digital-to-analog converter is used. If a clock is used, the same clock can be used to generate the sine and cosine waveforms (or alternatively the clock and 90 degree phase shifted clock) shown in FIG. 2c (block 203b), The clock used to generate the sine and cosine waveforms (or alternatively the clock and 90 degree phase shifted clock) may be in phase with the clock used for the differential voltage generator or may be a known phase shift from the clock used for the differential voltage generator. This is important in achieving an accurate calculation of the body impedance For the bio-impedance application, the magnitude and phase angle is obtained by using a mixer. The mixer is implemented having a single path for the in-phase and the quadrature phase. The input is multiplied by an in-phase clock and by a quadrature clock using the same path that is time multiplexed one after another. This allows for the mismatch in the paths for the in-phase and quadrature to be minimized. There is an input signal shift between the in-phase sampling and the quadrature sampling but since the signal bandwidth is so low this has minimal impact on accuracy compared to the mismatch between the two paths.

In some embodiments, the voltage generator will have a clock input to generate the waveform. This may be the case if a square wave is used or if a digital-to-analog converter is used (FIG. 1a, block 102a). If a clock is used, the same clock can be used to generate the sine and cosine waveforms (or alternatively the clock and 90 degree phase shifted clock) shown in FIG. 2a (block 202) and 2c (block 203b). The clock used to generate the sine and cosine waveforms (or alternatively the clock and 90 degree phase shifted clock) may be in phase with the clock used for the differential voltage generator or may be a known phase shift from the clock used for the differential voltage generator. This is important in achieving an accurate calculation of the body impedance.

As above described, the method and system allow for calculating bio-impedance using a sensor device. By inputting a voltage signal through known impedances and into a sensor device that has been placed on the body of a user, detecting the resultant output voltage signal, and processing the resultant output voltage using a combination of analog and digital signal processing, an accurate bio-impedance ($Z_{body}$) can be calculated utilizing a non-invasive and efficient system. The calculated bio-impedance ($Z_{body}$) can be utilized to determine and monitor a variety of health related values including the user's hydration level, respiration rate, and respiration depth.

A method and system for determining bio-impedance using a sensor device has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Further, one of ordinary skill in the art would recognize that the embodiments may be combined and/or substituted and those combination and/or substitution of embodiments would be within the spirit and scope of the present invention. Accordingly, many modifications may be made by one of ordinary skill in the art without departing from the spirit and scope of the appended claims.

What is claimed is:

1. A method for determining a bio-impedance of a user, comprising:
measuring a first voltage across a first impedance after performing a first mixing operation using a clock signal or sine wave;
measuring a second voltage across the first impedance after performing a second mixing operation using a 90-degree phase shifted clock signal or cosine wave;
measuring a third voltage at an output after performing a third mixing operation using the clock signal or sine wave;
measuring a fourth voltage at the output after performing a fourth mixing operation using the 90-degree phase shifted clock signal or cosine wave; and
processing the measured first through fourth voltages and the first impedance to at determine a bio-impedance.

2. The method of claim 1, wherein the cosine wave includes a 90-degree phase shifted from the sine wave.

3. The method of claim 1, wherein the first mixing process and the second mixing process are performed sequentially via a mixer using a single path to avoid an offset correction.

4. The method of claim 1,
wherein the first or the third voltage is multiplied by a first clock signal to generate a first or third output, respectively, and
wherein the second or the fourth voltage is multiplied by the 90-degree phase shifted clock signal from the first clock signal to generate a second or fourth output, respectively.

5. The method of claim 4, wherein the multiplication uses a same multiplier and a same path and the first through fourth mixing operations are performed sequentially in time.

6. The method of claim 1, wherein the processing comprises:
filtering the measured first through fourth voltages;
digitizing the measured first through fourth voltages;
processing the measured first through fourth voltages to remove at least one of noise or artifacts; and
mathematically combining the measured first through fourth voltages using an operation including at least one of: addition, subtraction, multiplication, or division with each other and coefficients.

7. The method of claim 6, wherein the filtering is performed by a low pass filter that performs at least one of: analog filtering, analog equalization, or amplification.

8. The method of claim 6, wherein the processing the output signal includes performing at least one of:
digital filtering using a decimation filter,
digital equalizing,
digital amplification,
artifact removal,
baseline wander removal, or
mathematically combining the measured first through fourth voltages using an operation including at least one of: addition, subtraction, multiplication, or division with each other and coefficients.

9. The method of claim 6, further comprising processing the output using user information including at least one of age, height, race, diet, weight, gender, or distance between the first and second electrode.

10. A bio-impedance front-end system, comprising:
a bio-impedance front-end receiver that:
performs a first mixing operation using a clock signal or sine wave,
performs a second mixing operation using a 90-degree phase shifted clock signal or cosine wave,
performs a third mixing operation using the clock signal or sine wave, and
performing a fourth mixing operation using the 90-degree phase shifted clock signal or cosine wave; and
a sensor device that:
measures a first voltage across a first impedance after the first mixing operation,
measures a second voltage across the first impedance after the second mixing operation,
measures a third voltage at an output after the third mixing operation using the clock signal or sine wave, and
measures a fourth voltage at the output after the fourth mixing operation using the 90-degree phase shifted clock signal or cosine wave; and wherein the bio-impedance front-end receiver processes the measured first through fourth voltages and the first impedance to calculate a bio-impedance.

\* \* \* \* \*